(12) United States Patent
Bauer

(10) Patent No.: US 9,814,626 B2
(45) Date of Patent: Nov. 14, 2017

(54) METHOD FOR PRODUCING BANDAGES

(71) Applicant: NTT NEW TEXTILE TECHNOLOGIES, Balingen (DE)

(72) Inventor: Hans Bauer, Balingen (DE)

(73) Assignee: NTT NEW TECHNOLOGIES GMBH, Balingen (DE)

(*) Notice: Subject to any disclaimer, the term of this patent is extended or adjusted under 35 U.S.C. 154(b) by 558 days.

(21) Appl. No.: 14/477,803

(22) Filed: Sep. 4, 2014

(65) Prior Publication Data

US 2014/0374943 A1    Dec. 25, 2014

Related U.S. Application Data

(63) Continuation-in-part of application No. PCT/EP2013/054342, filed on Mar. 5, 2013.

(30) Foreign Application Priority Data

Mar. 8, 2012    (DE) .................. 10 2012 101 937

(51) Int. Cl.
| | |
|---|---|
| *A61F 13/00* | (2006.01) |
| *A61F 13/08* | (2006.01) |
| *A61F 13/02* | (2006.01) |
| *A61F 13/10* | (2006.01) |
| *A61F 5/01* | (2006.01) |

(Continued)

(52) U.S. Cl.
CPC ...... *A61F 13/00987* (2013.01); *A61F 5/0106* (2013.01); *A61F 13/0286* (2013.01); *A61F 13/08* (2013.01); *A61F 13/102* (2013.01); *B29C 41/20* (2013.01); *A61F 2005/0176* (2013.01); *A61F 2013/00119* (2013.01); *B29K 2083/005* (2013.01); *B29K 2305/00* (2013.01);
(Continued)

(58) Field of Classification Search
CPC ............ A61F 13/00987; A61F 13/0286; A61F 13/00991; A61F 13/0279; B29C 65/522; B29C 70/025; B29C 70/028; B29C 70/023; B29C 41/20; Y10T 156/1089; Y10T 156/1092; Y10T 156/1093; Y10T 156/109; B05D 2350/60
USPC ................ 156/77–79, 297; 602/26; 427/412
See application file for complete search history.

(56) References Cited

U.S. PATENT DOCUMENTS 3,133,543 A *   5/1964   Bradd ...................... A41C 1/02
                                                    28/153
5,036,838 A *   8/1991   Sherman ................. A61F 13/06
                                                    128/DIG. 15

(Continued)

FOREIGN PATENT DOCUMENTS

| EP | 0 027 172 | 4/1981 |
|---|---|---|
| EP | 0 496 071 | 7/1992 |

(Continued)

*Primary Examiner* — John Goff
(74) *Attorney, Agent, or Firm* — Klaus J. Bach

(57) ABSTRACT

In a method for producing bandages such as support bandages for knee and elbow joints, an elastic fabric material layer is provided on which reinforcement elements are placed and an uncured elastomer is applied to the fabric material in several layers or sprayed onto the fabric material layer so as to completely cover and embed the reinforcement elements which are firmly engaged thereby with the fabric material layer and form three-dimensional stabilizing structures projecting from the surface of the fabric material layer.

9 Claims, 1 Drawing Sheet

(51) Int. Cl.
*B29C 41/20* (2006.01)
*B29K 83/00* (2006.01)
*B29K 305/00* (2006.01)
*B29L 31/00* (2006.01)

(52) U.S. Cl.
CPC ... *B29L 2031/753* (2013.01); *F04C 2270/041* (2013.01); *Y10T 156/1089* (2015.01)

(56) References Cited

U.S. PATENT DOCUMENTS 6,486,378 B1 * 11/2002 Areskoug ........... A61F 13/0203
602/41
2010/0173119 A1 * 7/2010 Vitarana ................ D04H 11/00
428/90

FOREIGN PATENT DOCUMENTS

EP 1 086 669 3/2001
WO WO 2011/007179 1/2011

* cited by examiner

METHOD FOR PRODUCING BANDAGES

This is a Continuation In Part application of pending international patent application PCT/EP2013/05432 filed Mar. 5, 2013 and claiming the priority of German patent application 10 2012 101 937.1 filed Mar. 8, 2012.

BACKGROUND OF THE INVENTION

The invention resides in a method for producing bandages, in particular joint bandages such as knee and elbow bandages.

Joint bandages consisting of an elastic woven material on which a pre-manufactured silicon molded part is applied by cementing, welding or stitching are known. The molded parts provide for additional stability and for a better support of the joint around which the bandage is wound like a cuff. The molded part extends for example annularly around the elastic fabric material layer and is connected to the fabric material layer. A second fabric material layer may cover the molded part.

For the manufacture of such bandages, several manufacturing steps are required. First, the molded part of silicone has to be manufactured, then the molded part is connected to the fabric material layer and, finally, the additional material layer needs to be applied.

DE 601 04 663 T2 discloses an orthopedic article such as an orthopedic sole using a block of silicone elastomer to which a textile material is applied. Herein, first one side of the textile material is coated by a two-component silicone cement and subsequently the coated side of the textile material is placed onto the pre-manufactured block of silicone elastomer. Then the combination of the textile material and the block of silicone elastomer is heated for a predetermined time to an increased temperature in order to achieve a cross-linking of the silicone cement.

It is the object of the present invention to provide a bandage in a flexibly manageable and simple manner which bandage is provided with a supportive molded part.

SUMMARY OF THE INVENTION

In a method for producing bandages such as support bandages for knee and elbow joints, an elastic fabric material layer is provided on which reinforcement elements are placed and an uncured elastomer material is applied to the fabric material in several layers or sprayed onto the fabric material layer so as to completely cover and embed the reinforcement elements which are firmly engaged thereby with the fabric material layer and form three-dimensional stabilizing structures projecting from the surface of the fabric material layer.

The bandage provides for improved support of the joints, the tendons or muscle parts. The molded part consists of an elastomer which is applied to the flexible fabric material layer in a non-cured, gooey or at least deformable state. The non-cured elastomer can enter the fabric material layer and join the fabric material layer so that no further procedures are needed for joining the molded part and the fabric material layer. With the application of the elastomer to the fabric material layer in an uncured state and the subsequent curing, a sufficiently rigid connection between the fabric material layer and the molded part of elastic material is established.

In comparison with state of the art methods, several manufacturing steps are eliminated with the method according to the invention. With the application of the elastomer to the fabric layer, the molded part is produced and at the same time connected to the fabric layer. No additional procedures are required for the connection of the molded part with the fabric layer; in particular, no cement is needed for connecting the elastomer molded part to the fabric material layer. In the non-cured state, in which the elastomer is applied to the fabric layer, it can be sufficiently shaped so that the molded part can be brought into the desired form. At the same time, the elastomer is sufficiently viscous to prevent it from flowing off or at least this is minimized so that the desired three-dimensional shapes can be provided. In the cured state, the molded part which consists of elastomer, has a sufficiently high elasticity to provide together with the elastic fabric layer, a bandage with the required stability and elasticity.

The elastomer by which the molded part is established may be a strongly adhesive silicone which, upon application of the bandage comes into direct contact with the skin and has the effect of a medical wound treatment or surgical dressing. By an attachment to the skin, the position of the bandage is also secured.

The elastomer is applied preferably by a spraying process. Herein, the uncured elastomer is sprayed onto the fabric material layer and cured thereon. In a non-cured state, the elastomer has a sufficiently high viscosity which permits spraying thereof onto the fabric material layer.

The spraying is performed preferably via a nozzle which has the advantage that the elastomer can be applied to the fabric material layer with high precision.

In accordance an expedient embodiment, the elastomer is applied in the form of layers. Upon application of a layer, the elastomer cures at least partially and therefore develops an increased rigidity whereupon the next layer of elastomer can be applied. In this way, the elastomer is applied by spraying layer by layer, until the desired three-dimensional shape of the molded, part has been reached. After the application of each layer, the elastomer is permitted to cure at least partially before the next layer is applied.

In accordance with a further expedient embodiment, the elastomer is applied or, respectively sprayed directly onto the fabric material layer, whereby the need for a cement for its connection to the fabric material layer is omitted.

It may also be advantageous if, after application of the elastomer to the fabric material layer, a flock coating is applied which will improve the comfort of the wearer. The flock coating may be applied to the elastomer before it is fully cured so that the flock coating material is firmly attached to the molded part upon curing of the elastomer. No cement is needed for the connection of the flock coating material to the elastomer. Basically, however, the flock coating may also be applied later to the already cured molded part by using expediently a cement for the attachment of the flock coating to the molded part. As flock coating material natural fibers, synthetic fibers or semi-synthetic fibers may be used.

The elastomer is preferably applied only to one side of the fabric material layer so that the molded elastomer part projects from the fabric layer three-dimensionally only from this side. The flock coating occurs preferably also only on the side where the molded part project. However, flock coating may also be applied at the opposite side as far as the elastomer material passes through the fabric material layer while it is still uncured.

In accordance with another expedient embodiment, an elastomer material is applied to both sides of the fabric material layer for providing a molded part wherein the molded parts are arranged either mirror-reversed relative to each other or have different positions and/or geometries.

It may be expedient, to embed a reinforcement element into the elastomer material in order to provide a greater stability to the molded part. Furthermore, the reinforcement element permits a three-dimensional height build-up of the molded part which may be shaped in any way as it can be established by an elastomer bead while the elastomer is not yet cured. The reinforcement element is advantageously covered by spray coating.

As reinforcement element, for example, a foamed material part may be used which has a desired basic shape which is then adopted by the elastomer part. The foamed material part is covered by still uncured elastomer which subsequently hardens, whereby by the elasticity of the elastomer and the foamed part jointly provide for the desired elastic properties.

As reinforcement element also a component consisting of metal, plastic, ceramics or similar may be used, which in addition to shaping function have also a reinforcement function. It is for example possible to embed springs into the elastomer to form reinforcement elements which provide for the molded part and the fabric material layers a certain desired spring effect.

As elastomer for example silicon is used, which, in an uncured state, has a viscosity that permits its spraying onto the fabric material layer or, respectively, the reinforcement element via a spray nozzle. The nozzle spray application has the advantage that the elastomer can be applied to the fabric material layer in a highly precise manner. Also a layer buildup of the molded part with different superimposed elastomer layers can be provided by the spray application via a spray nozzle in a precise manner.

Expediently, the reinforcement element is not directly amended to the fabric material layer. It is preferably attached exclusively by the elastomer in which the reinforcement element is embedded. It is not necessary that the reinforcement element is cemented to the fabric material layer.

Basically, the elastomer or, respectively, the molded part may be arranged on the fabric material layer in various ways. The molded part may for example be arranged in spaced relationship from the edge of the fabric material layer wherein also embodiments are possible in which the molded part extends up to the edge area of the fabric material layer.

The invention will become more readily apparent from the following description of a particular embodiment thereof with reference to the accompanying drawings.

DETAILED DESCRIPTION OF A PARTICULAR EMBODIMENT

Figure 1:
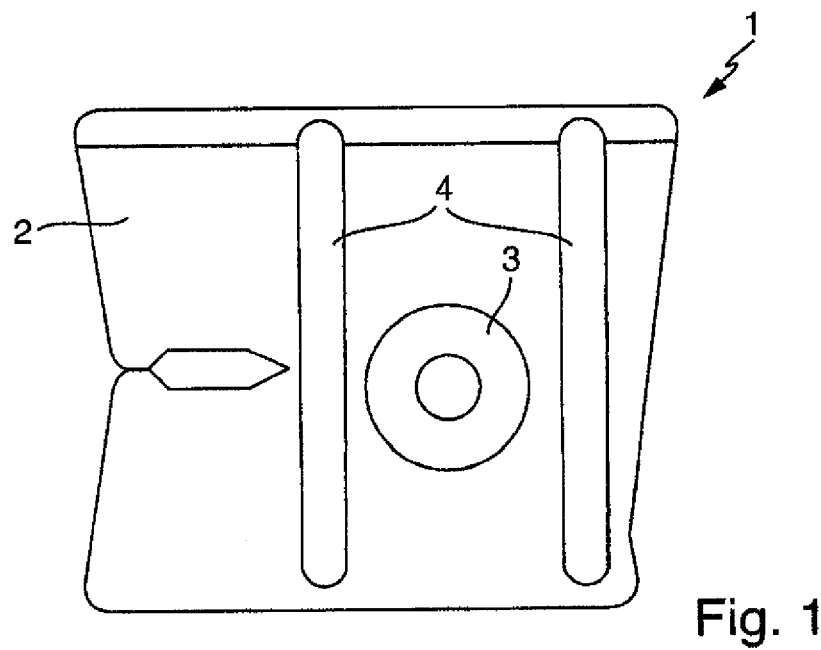
FIG. 1 is a top view of a bandage which includes a fabric material layer to which elastic molded parts of silicone are applied.

In the figures, identical components are designated by the same reference numerals.

Figure 2:
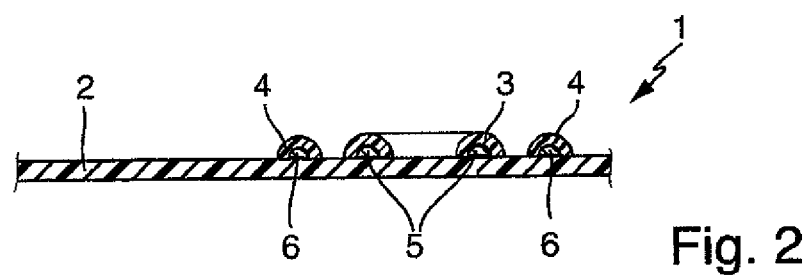
FIG. 2 is a cross-sectional view of the bandage shown in FIG. 1.

FIGS. 1 and 2 show a joint bandage 1 in a top view and, respectively, a cross-sectional view. The joint bandage 1 is for example a knee bandage or an elbow bandage which may be wound around the leg or arm and fixed in position for supporting the respective joint. The bandage 1 comprises an elastic fabric material layer 2 on which molded parts 3 and 4 are disposed for reinforcement of the bandage and to support the joint when wound around it. The first molded part 3 is an annular projection 3, and the two mold parts 4 at opposite sides of the annular projection 3 are rod-like projections.

The molded projections 3 and 4 each consist of an elastomer, such as silicon material into which a reinforcement element 5, 6 is embedded. The elastomer is applied to the fabric material layer 2 in an uncured flowable state. The reinforcement elements 5, 6 are disposed on the fabric material layer and the elastomer material is sprayed over the reinforcement elements 5, 6. After the hardening or, respectively, curing of the elastomer, the reinforcement elements 5, 6 are completely enclosed by the elastomer. During the manufacturing process, the elastomer material penetrates into the fabric material layer 2 and, upon curing, provides for a connection of the molded part 3, 4 with the fabric layer 2. Since the reinforcement elements are embedded in the elastomer layer 3, 4, the reinforcement elements 5, 6 are firmly engaged with the fabric material layer 2.

As apparent from the sectional view of FIG. 2, the molded projections 3, 4 are three-dimensionally shaped elastic support structures which project from one side of the fabric material layer 2. The shaping is achieved essentially by the reinforcement elements 5, 6. Since the reinforcement elements are completely surrounded by the elastomer material the overall height and width of the molded projections 3 and 4 is greater than those of the reinforcement elements 5, 6.

Figures 3, 4:
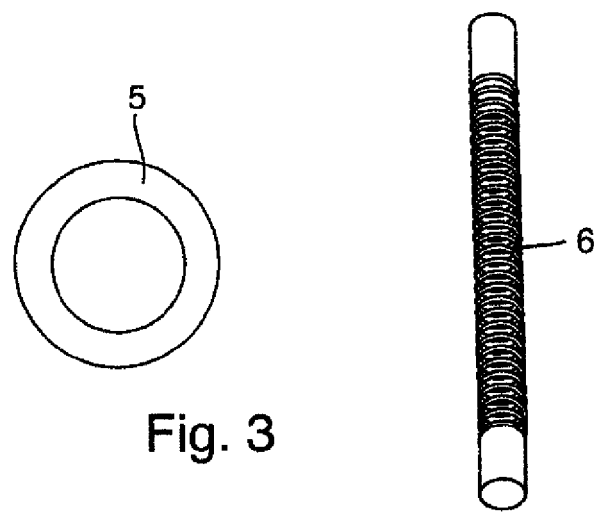
FIG. 3 shows an annular reinforcement element of a foamed material which is embedded into the silicone during manufacture.
FIG. 4 shows a rod-shaped spring element of metal which may also be embedded into silicone on top of the fabric material layer.

As shown in FIGS. 3 and 4, the reinforcement element 5 is an annular foamed component and the reinforcement element 6 is a rod-shaped metal spring element which is resiliently bendable. The foam element is also elastically resilient. As a result of the elasticity or, respectively, bendability of the reinforcement elements 5, 6 and the inherent elasticity of the cured, hardened elastomer material as well as the elasticity of the fabric material layer 2, it is ensured that the bandage 1 has a relatively high stability. By the reinforcement elements furthermore a predetermined directional stability can be provided for example in that the rod-shaped spring element 6 is bendable only about its transverse axis but has essentially no elasticity in the direction of the longitudinal axis thereof.

The reinforcement elements 5, 6 are disposed during manufacture only loosely on the fabric material layer 2. Their connection to the fabric material layer is obtained by the molded part 3 which consists of elastomer material which penetrates into the fabric material layer 2 where it is cured.

The molded projections 3, 4 are expediently covered by a flock coating in order to improve the wearing comfort. The flock coating material comprises organic, synthetic or semi-synthetic fibers which are for example applied before the elastomer material is cured so that the flock coating material is firmly attached to the elastomer material. But the flock coating may also be applied after the curing of the elastomer material, wherein, however, in this case, additionally cement is being used.

For the manufacture of the bandage, first the molded parts 3 and 4 are placed onto the fabric material layer 2. The uncured elastomer material which as silicone is sprayed via one or more nozzles onto the fabric material layer 2 so as to completely embed the reinforcement elements 5, 6 into the elastomer material, whereupon the elastomer material hardens. Before the hardening however, preferably the flock coating is applied.

What is claimed is:

1. A method for producing bandages (1) for knee and elbow joints, comprising the steps of: providing an elastic fabric material layer (2), placing reinforcement elements (5, 6) in predetermined positions onto one side of the elastic fabric material layer (2), covering the elastic fabric material layer with the reinforcement elements (5, 6) disposed thereon with several layers of elastomer coatings by spraying a first uncured elastomer coating in a liquid or gooey state onto the elastic fabric material layer (2) so as to embed the reinforcement elements (5, 6) disposed on the elastic fabric material layer (2), while penetrating into the elastic fabric material layer (2) each additional coating being applied to a previously applied layer when the previously applied coating is only partially cured and fully curing the elastomer coatings embedding the reinforcement elements (5, 6) to firmly engage the reinforcement elements (5, 6) with the elastic fabric material layer (2) and forming three-dimensional molded areas (3,4) projecting from the one side of the fabric material layer (2).

2. The method according to claim 1, wherein, after the elastomer coatings are sprayed onto the elastic fabric material layer (2), a flock coating is applied to the elastomer material.

3. The method according to claim 2, wherein the flock coating is applied before the last sprayed-on elastomer coating is fully cured.

4. The method according to claim 1, wherein the elastomer coatings are silicone material coatings.

5. The method according to claim 1, wherein the elastomer coatings are applied in spaced relationship from opposite end edges of the fabric material layer (2).

6. The method according to claim 1, wherein the elastomer coatings are applied to the fabric material layer without additional cement.

7. A method according to claim 1, wherein the reinforcement elements (5, 6) comprise spaced rod-shaped elements (6) with annular element (5) disposed between the spaced rod-shaped reinforcement elements.

8. A method according to claim 7, wherein the rod-shaped reinforcement elements (6) are metal spring elements and the annular reinforcement elements (5) are formed of an elastically resilient material.

9. A method for producing bandages for knee and elbow joints, comprising the steps of: providing an elastic fabric material layer (2), placing straight reinforcement elements (5) on opposite sides of an annular reinforcement element (6) in spaced relationship in predetermined positions onto the elastic fabric material layer (2), applying successively uncured elastomer material in several layers to the elastic fabric material so as to cover the reinforcement elements (5, 6) so that the elastomer material at least partially penetrates the fabric material layer (2), and curing the elastomer, material thereby firmly engaging the reinforcement elements (5, 6) with the fabric material layer thereby forming three-dimensional molded areas (3, 4) projecting from the surface of the fabric material layer (2).

* * * * *